(12) United States Patent
Godfried et al.

(10) Patent No.: US 6,507,396 B1
(45) Date of Patent: Jan. 14, 2003

(54) SPECTROSCOPIC ANALYZING ARRANGEMENT

(76) Inventors: Herman Philip Godfried, Dalkruid 57, NL-7491, LP Delden (NL); Herman Hubertus Jacobus Reijnen, Hoogeindsestraat 26, NL-5447, PE Rijkevoort (NL); Willem Kornelis Leendert Van Der Voorden, Burghardt Van der Berghstraat 151, NL-6512, NK Nijmegen (NL)

(*) Notice: Subject to any disclaimer, the term of this patent is extended or adjusted under 35 U.S.C. 154(b) by 0 days.

(21) Appl. No.: 09/719,902

(22) PCT Filed: Jun. 18, 1999

(86) PCT No.: PCT/IB99/01147

§ 371 (c)(1),
(2), (4) Date: Mar. 28, 2001

(87) PCT Pub. No.: WO99/66312

PCT Pub. Date: Dec. 23, 1999

(30) Foreign Application Priority Data

Jun. 18, 1998 (ZA) .................................................. 98/5299

(51) Int. Cl.[7] .................................................. G01J 3/00
(52) U.S. Cl. .................................. 356/300; 250/339.11
(58) Field of Search ....................... 356/300; 250/339.11

(56) References Cited

U.S. PATENT DOCUMENTS

| 4,303,859 A | 12/1981 | McCue |
| 5,773,825 A | 6/1998 | Doyle |

FOREIGN PATENT DOCUMENTS

| DE | 43 33 560 A1 | 4/1995 | |
| EP | 0 624 785 A1 | 9/1993 | |
| JP | 06-273323 A | * 9/1994 | ................. 356/300 |

* cited by examiner

Primary Examiner—Cassandra Spyrou
Assistant Examiner—Fayez Assaf
(74) Attorney, Agent, or Firm—Scully, Scott, Murphy & Presser

(57) ABSTRACT

A spectroscopic analyzing arrangement comprises an ATR optical sampling plate with a front sample-contacting face and an opposed rear internally face. An anvil assembly is arranged so that the sample-contacting face can be pressed against the sample to receive spectroscopic information. A reflection barrier between the anvil assembly and the rear face prevents internally reflected light within the sampling plate from picking up spectroscopic information from the anvil assembly, thus enhancing the performance of the arrangement.

14 Claims, 2 Drawing Sheets

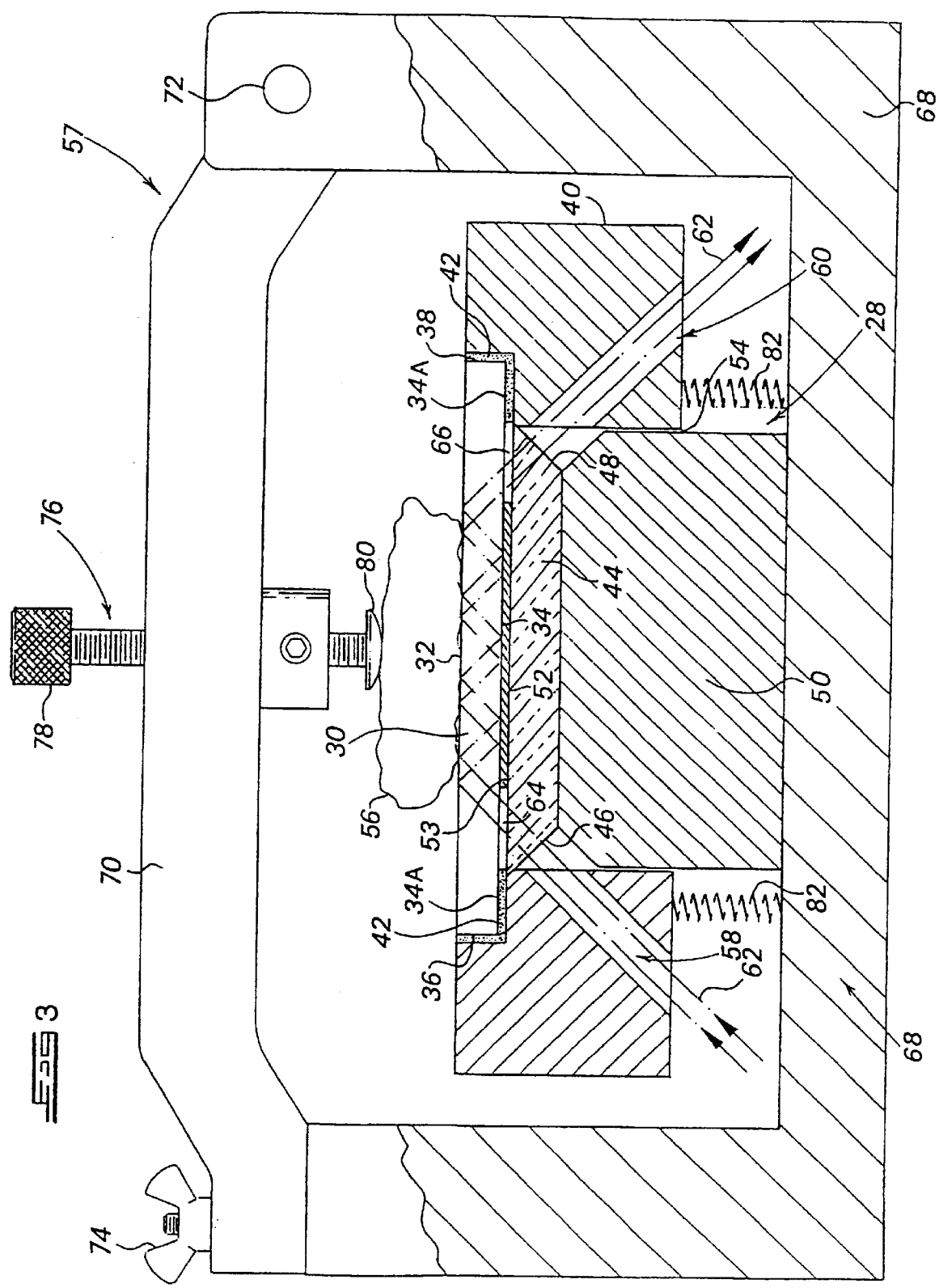

US 6,507,396 B1

SPECTROSCOPIC ANALYZING ARRANGEMENT

FIELD OF THE INVENTION

THIS invention relates to a spectroscopic analyzing arrangement which incorporates an optical device for multi-bounce attenuated total reflection (ATR) spectroscopic analysis.

SUMMARY OF THE INVENTION

According to the invention there is provided a spectroscopic analyzing arrangement comprising an ATR optical sampling plate having a front sample-contacting face, and an opposed rear internally reflecting face, an anvil assembly located rearwardly of the rear reflecting face for allowing the sample-contacting face to be pressed sufficiently hard against the sample to receive spectroscopic information therefrom, and a reflection barrier located between the anvil assembly and the rear internally reflecting face of the sampling plate for preventing internally reflected light within the sampling plate from picking up spectroscopic information from the anvil assembly.

In a preferred form of the invention, the anvil assembly comprises an anvil and a prism having an entry facet for receiving incident light and an exit facet for allowing light reflected within the sampling plate to exit, the prism having a front face arranged to make contact with the rear reflecting face of the sampling plate via the reflection barrier and an opposed rear face against which the anvil locates.

Conveniently, an outer peripheral support is fixed to the outer periphery of the sampling plate, preferably by gluing or brazing, with entry and exit passages being defined in the outer peripheral support for receiving the incident and reflected light beams.

Both the sampling plate and the prism are typically formed from a diamond material such as a type IIA or a CVD diamond.

The reflection barrier is conveniently in the form of a reflective metallic coating having a maximum thickness of 10% of the wavelength of light used.

The coating is preferably coated onto the front face of the prism but may also be applied directly to the rear internally reflecting face of the sampling plate, if it allows good internal reflection from its adhesion layer.

BRIEF DESCRIPTION OF THE DRAWINGS

FIG. 3 shows a partly schematic cross-sectional side view of a multi-bounce ATR spectroscopic analyzer of the present invention.

DESCRIPTION OF BACKGROUND

Figure 1:
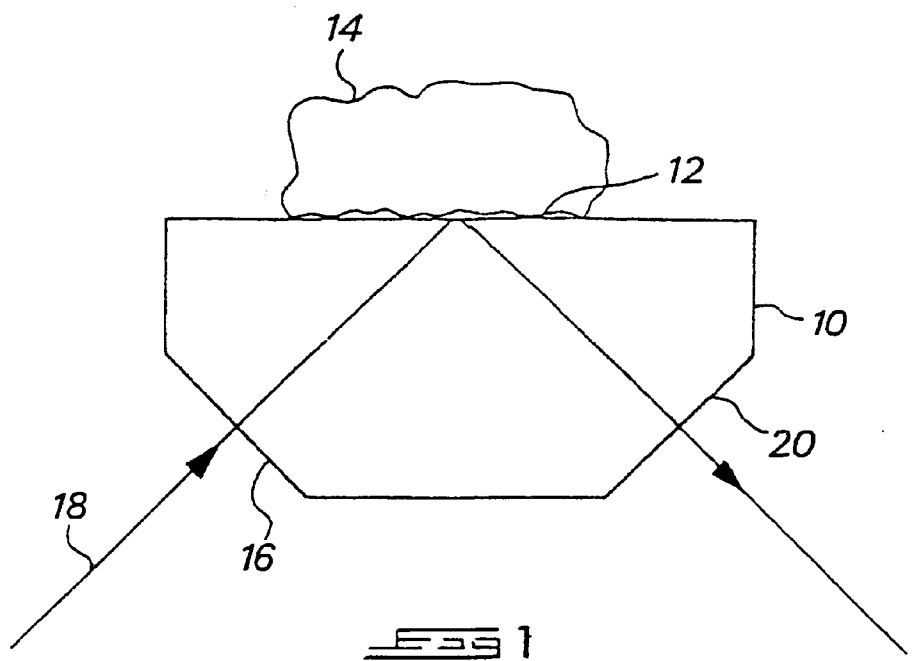
FIG. 1 shows a highly schematic view of a prior art single bounce ATR prism.

Referring first to FIG. 1, a simple single-bounce prism 10 is shown having a front contact surface or facet 12 which contacts a sample 14. The prism 10 is also provided with an angled entry facet 16 for receiving a beam of light 18 which reflects off the contact surface 12 and exits through an exit facet 20 for subsequent spectroscopic analysis. The described arrangement makes use of attenuated total reflection (ATR) spectroscopic analysis, which depends on the fact that a beam of light which is reflected from a contact surface 12 between an optical medium 10 and a sample 14 carries spectroscopic information from that sample.

Figure 2:
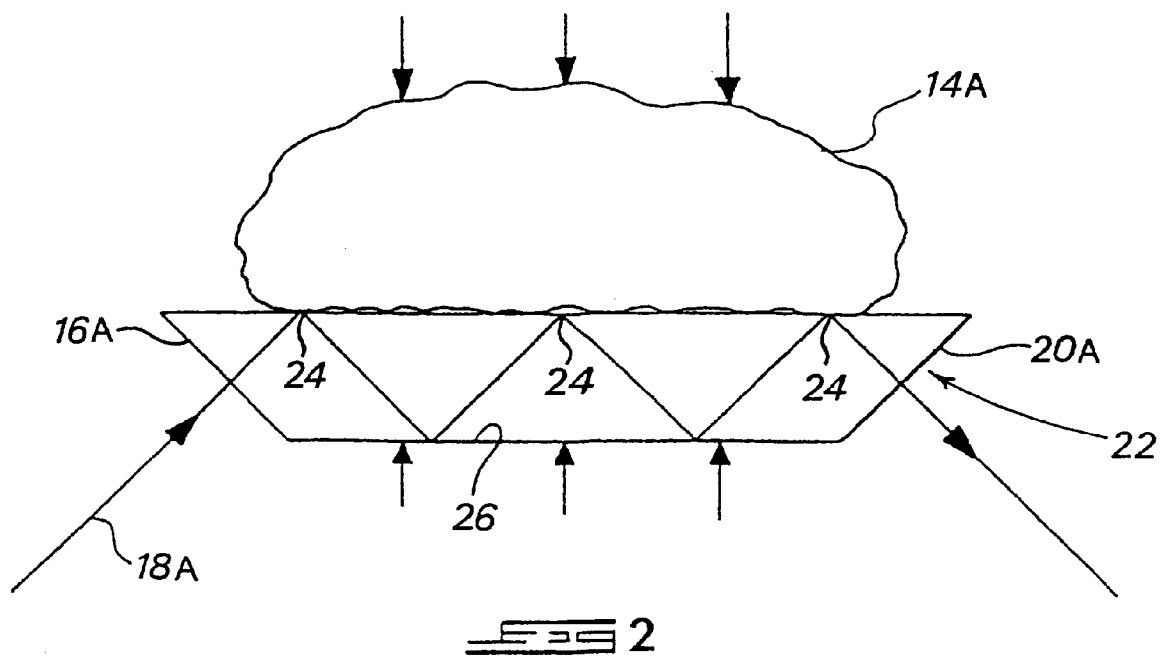
FIG. 2 shows a highly schematic view of a prior art multi-bounce ATR prism.

In FIG. 2, a prior art multi-bounce prism 22 is shown which operates on the same principles as the single-bounce prism 10 of FIG. 1, save that repeated reflections 24 of the light beam 18A off the sample 14A result in a better spectroscopic signal carrying additional information from the sample 14A. In addition to the entry and exit facets 16A and 20A, the multi-bounce prism 22 is also provided with a rear total internal reflection facet 26 for allowing total internal reflection of the light beam 18A prior to its exit.

Critical to the ATR process is the provision of intimate optical contact between the sample and the prism. In the case of a liquid sample, this is easily achieved, but in order to achieve good optical contact with the solid sample, the sample needs to be pressed against the prism with not insubstantial force via a mechanical load. In the more effective multi-bounce arrangement illustrated in FIG. 2, the thickness of the prism is generally chosen in the range of 0.3 mm to 2 mm. with the prism having a corresponding length varying from 1 mm to 10 mm. The fairly long and thin strip which results has a delicate construction which is not easily capable of absorbing the required contact force in the case of a solid sample.

An obvious way of coping with the resultant mechanical load, is to provide a direct support for the rear face 26 of the prism. A significant disadvantage of this apparent solution is that the support itself will, by virtue of its intimate optical contact with the face 26, add its own unwanted spectroscopic information to the light beam. In addition, support of the entry and exit facets of the prism is not easily achievable as this would tend to result in some form of interference with the entry and exit light beams.

DESCRIPTION OF AN EMBODIMENT

Referring now to FIG. 3, a multi-bounce ATR spectroscopic analyzing arrangement of the invention is shown which aims to overcome the aforementioned problems associated with the FIG. 1 and FIG. 2 prior art structures. The arrangement includes a front optical sampling plate 30 formed from a type IIA or CVD diamond and having a substantially rectangular profile, with a front contact face 32, an opposed rear reflecting face 34 and end faces 36 and 38. A peripheral plate bolder or mount 40 is brazed or glued at 42 to the outer periphery of the plate constituted by the end faces 36 and 38 and the outer peripheral zones 34A of the rear face 34. A prism 44 similarly formed from a type IIA or CVD diamond has angled entry and exit facets 46 and 48 is sandwiched between the plate 30 and an anvil 50, which fits snugly within an opening 54 defined by the outer peripheral support 40. A reflection barrier 52 is provided between the rear face 34 of the sampling plate and the front face 53 of the prism. The anvil 50 may in itself constitute the mechanical load so as to ensure that sufficient pressure is exerted between the optical plate 30 and the sample 56. Alternatively, an external force may be applied to the anvil, or the anvil may serve as a mount for securing adjustable clamping means in the form of a clamping assembly 57 which passes around the sample 56 and allows the sample to be clamped firmly against the contact surface 32 of the plate 30.

Entry and exit passages 58 and 60 are defined in the peripheral mount or support 40 and provide respective travel paths for incident and reflected light beams 62 and 62A. The reflection barrier 52 also stops short of the incident and reflected paths. In order to eliminate unwanted reflections at the entry and exit interfaces 64 and 66 of the rear surface of the plate 30 and the front surface of the prism 44, the thickness of the reflection barrier 52, and thus the distance between the sampling plate 30 and the prism 44, is minimized to less than 10% of the wavelength of the light used. The reflection barrier or mirror 52 is typically constituted by a reflective coating of a titanium adhesion layer which is coated onto the prism 44 and an overlying reflective gold layer having a total thickness of 100 to 200 nanometers (which corresponds to not more than one tenth of the wavelength of the incident light beam). The reflection barrier 52 is coated onto the prism 44 so that the adhesion layers between the coating and the prism do not influence the light beam as it is reflected off the rear surface 34 of the plate. In high temperature applications, a platinum diffusion barrier may be provided between the titanium and gold layers.

In the prototype, it was found that background light entering the prism 44 through the entry face 46 and exiting through the exit face 48 resulted in unwanted background noise. The elimination of this background light is addressed in a number of ways. Firstly, the titanium adhesion layer which is coated onto the prism 44 and the overlying reflective gold layer act as a background light absorbing layer for the top of the prism 44. A layer of epoxy, an absorbent coating or a black carbon layer can be added to the bottom surface of the prism 44 to act as a further background light absorber.

Alternatively, or in addition, the top and bottom surfaces of the prism 44 are corrugated to obtain diffusely reflecting surfaces for background light, or the top and bottom surfaces of the prism 44 can have small grooves to stop the incident light by reflection.

Finally, the prism 44 may be split into two parts with a light barrier, which may be, for example, metal foil, inserted between the two parts. In this variation, the prism will be joined together by, for example, gluing.

The clamping assembly 57 comprises a U-shaped yoke 68, and a clamping arm 70 is hinged at 72 to one arm of the yoke, with the opposed free end of the clamping arm being screwed to the opposite arm of the yoke by means of a clamping screw 74. A loading screw 76 passes through the centre of the clamping arm 70 and is formed with a finger grip 78 and an opposed head 80 for applying pressure directly onto the rear face of the sample 56 as the loading screw 76 is turned. Preferably, the anvil 50 sits on or is mounted directly to the base of the yoke, and the support 40 is mounted to the base of the yoke via flexible mounts in the form of springs 82. Alternatively the anvil 50 and the support 40 are joined together by, for example, gluing or brazing.

The dimensions, shapes and angles of both the sampling plate 30 and the prism 44 may vary considerably depending on the number of optical bounces required. For instance, circular or disc-shaped prisms and plates may also be provided, with corresponding alterations being made in the configuration of the other components making up the spectroscopic analysis arrangement.

What is claimed is:

1. A spectroscopic analyzing arrangement comprising an ATR optical sampling plate having a front sample-contacting face and an opposed rear internally reflecting face, an anvil assembly located rearwardly of the rear reflecting face for allowing the sample-contacting face to be pressed sufficiently hard against the sample to receive spectroscopic information therefrom, and a reflection barrier located between the anvil assembly and the rear internally reflecting face of the sampling plate for preventing internally reflected light within the sampling plate from picking up spectroscopic information from the anvil assembly, characterised in that the anvil assembly comprises an anvil and a prism having an entry facet for receiving incident light which is directed to the sampling plate and an exit facet for allowing light reflected within the sampling plate to exit, the prism having a front face arranged to make contact with the rear reflecting face of the sampling plate via the reflection barrier and an opposed rear face against which the anvil locates.

2. A spectroscopic analyzing arrangement according to claim 1 wherein an outer peripheral support is fixed to the outer periphery of the sampling plate with entry and exit passages being defined in the outer peripheral support for receiving the incident and reflected tight beams.

3. A spectroscopic analyzing arrangement according to claim 2 wherein the outer peripheral support is fixed to the outer periphery of the sampling plate by gluing or brazing.

4. A spectroscopic analyzing arrangement according to any one of claim 1 wherein both the sampling plate and the prism are formed from a diamond material.

5. A spectroscopic analyzing arrangement according to claim 4 wherein the diamond material is a type IIA or a CVD diamond.

6. A spectroscopic analyzing arrangement according to claim 1 wherein the reflection barrier is in the form of a reflective metallic coating having a maximum thickness of 10% of the wavelength of light used.

7. A spectroscopic analyzing arrangement according to claim 6 wherein the coating is applied onto the front face of the prism.

8. A spectroscopic analyzing arrangement according to claim 6 wherein the coating is applied directly to the rear internally reflecting face of the sampling plate.

9. A spectroscopic analyzing arrangement according to claim 1 further comprising a background light absorbing layer applied to the bottom surface of the prism.

10. A spectroscopic analyzing arrangement according to claim 9 wherein the background light absorbing layer is a layer of epoxy, an absorbent coating or a black carbon layer.

11. A spectroscopic analyzing arrangement according to claim 1 wherein the top and bottom surfaces of the prism are corrugated to obtain a diffusely reflecting surface for background light.

12. A spectroscopic analyzing arrangement according to claim 1 wherein the top and bottom surfaces of the prism are grooved to stop incident background light by reflection.

13. A spectroscopic analyzing arrangement according to claim 1 wherein the prism is split into two parts with a background light barrier inserted between the two parts.

14. A spectroscopic analyzing arrangement according to claim 13 wherein the background light barrier is metal foil.

* * * * *